(12) United States Patent
Levy

(10) Patent No.: US 10,568,865 B2
(45) Date of Patent: Feb. 25, 2020

(54) WATER SOLUBLE COMPOSITIONS COMPRISING PURIFIED CANNABINOIDS

(71) Applicant: CANOPY GROWTH CORPORATION, Smith Falls (CA)

(72) Inventor: Kurt Aron Levy, Superior, CO (US)

(73) Assignee: Canopy Growth Corporation, Ontario (CA)

( * ) Notice: Subject to any disclaimer, the term of this patent is extended or adjusted under 35 U.S.C. 154(b) by 0 days.

(21) Appl. No.: 16/328,833

(22) PCT Filed: Aug. 29, 2017

(86) PCT No.: PCT/US2017/049219
§ 371 (c)(1),
(2) Date: Feb. 27, 2019

(87) PCT Pub. No.: WO2018/044953
PCT Pub. Date: Mar. 8, 2018

(65) Prior Publication Data
US 2019/0183853 A1 Jun. 20, 2019

Related U.S. Application Data

(60) Provisional application No. 62/380,954, filed on Aug. 29, 2016.

(51) Int. Cl.

| A61K 31/335 | (2006.01) |
|---|---|
| A61K 31/355 | (2006.01) |
| A61K 31/353 | (2006.01) |
| A61K 9/107 | (2006.01) |
| A61K 31/352 | (2006.01) |
| A61K 9/08 | (2006.01) |
| A61K 31/015 | (2006.01) |
| A61K 31/045 | (2006.01) |
| A61K 31/122 | (2006.01) |
| A61K 31/192 | (2006.01) |
| A61K 31/01 | (2006.01) |
| A61K 47/22 | (2006.01) |
| A61K 36/185 | (2006.01) |
| A61K 31/105 | (2006.01) |
| A61K 45/06 | (2006.01) |
| A61K 31/065 | (2006.01) |

(52) U.S. Cl.
CPC .............. *A61K 31/353* (2013.01); *A61K 9/08* (2013.01); *A61K 9/107* (2013.01); *A61K 31/01* (2013.01); *A61K 31/015* (2013.01); *A61K 31/045* (2013.01); *A61K 31/065* (2013.01); *A61K 31/105* (2013.01); *A61K 31/122* (2013.01); *A61K 31/192* (2013.01); *A61K 31/352* (2013.01); *A61K 31/355* (2013.01); *A61K 36/185* (2013.01); *A61K 45/06* (2013.01); *A61K 47/22* (2013.01)

(58) Field of Classification Search
CPC ............................ A61K 31/335; A61K 31/355

USPC .................................................. 514/454, 458
See application file for complete search history.

(56) References Cited

U.S. PATENT DOCUMENTS

| 4,837,228 | A | 6/1989 | Elsohly et al. | |
|---|---|---|---|---|
| 6,982,282 | B2 * | 1/2006 | Lambert | .............. A61K 9/0019 |
| | | | | 424/405 |
| 7,923,026 | B2 | 4/2011 | Moschwitzer | |
| 8,790,719 | B2 | 7/2014 | Parolaro et al. | |
| 2003/0101902 | A1 | 6/2003 | Reitnauer et al. | |
| 2006/0257463 | A1 | 11/2006 | Elsohly et al. | |
| 2008/0193725 | A1 | 8/2008 | Saint-Romain | |
| 2009/0098192 | A1 | 4/2009 | Fuisz | |
| 2009/0133704 | A1 | 5/2009 | Strickland et al. | |
| 2010/0298579 | A1 | 11/2010 | Steup et al. | |
| 2011/0052694 | A1 | 3/2011 | Stinchcomb et al. | |
| 2012/0004251 | A1 | 1/2012 | Whalley et al. | |
| 2013/0059018 | A1 | 3/2013 | Parolaro et al. | |
| 2013/0276779 | A1 | 10/2013 | Hale et al. | |
| 2014/0100269 | A1 | 4/2014 | Goskonda et al. | |
| 2014/0221469 | A1 | 8/2014 | Ross et al. | |
| 2014/0243405 | A1 | 8/2014 | Whalley et al. | |
| 2014/0271940 | A1 | 9/2014 | Wurzer et al. | |
| 2015/0064250 | A1 | 3/2015 | Ghebre-Sellassie et al. | |
| 2015/0126595 | A1 | 5/2015 | Smith et al. | |
| 2015/0258040 | A1 | 9/2015 | Lynch et al. | |
| 2015/0297556 | A1 | 10/2015 | Smith | |
| 2016/0029658 | A1 | 2/2016 | Segawa et al. | |

(Continued)

FOREIGN PATENT DOCUMENTS

| CA | 2684562 | 10/2008 |
|---|---|---|
| GB | 2495118 | 4/2013 |

(Continued)

OTHER PUBLICATIONS

International Search Report and Written Opinion prepared by the ISA/U.S. Patent and Trademark Office dated Oct. 12, 2017, for International Application No. PCT/US2017/049219.

Ansel et al., "Pharmaceutical Dosage Forms and Drug Delivery Systems, 7th Edition," Lippincott, Williams, & Wilkins, 1999, pp. 48-53.

Chen, "Some of the Parts: Is Marijuana's 'Entourage Effect' Scientifically Valid?" Scientific American, Apr. 20, 2017, retrieved from www.scientificamerican.com/article/some-of-the-parts-is-marijuana-rsquo-s-ldquo-entourage-effect-rdquo-scientifically-valid/, 3 pages.

Izzo et al., "Inhibitory effect of cannabichromene, a major non-psychotropic cannabinoid extracted from Cannabis sativa, on inflammation-induced hypermotility in mice," British Journal of Pharmacology, vol. 166, 2012, pp. 1444-1460.

(Continued)

*Primary Examiner* — Raymond J Henley, III
(74) *Attorney, Agent, or Firm* — Sheridan Ross P.C.

(57) ABSTRACT

This disclosures relates to new compositions and methods for making cannabinoid formulations. In one embodiment, this disclosure provides water soluble compositions comprising a first purified cannabinoid and Vitamin E TPGS. In one embodiment, the disclosure herein comprises a method of making powders comprising heatings material to a first temperature and a second temperature.

14 Claims, No Drawings

(56) References Cited

U.S. PATENT DOCUMENTS

| | | | |
|---|---|---|---|
| 2016/0081976 A1* | 3/2016 | Bromley | A61K 31/355 424/456 |
| 2016/0250270 A1 | 9/2016 | Wendschuh et al. | |
| 2016/0256395 A1 | 9/2016 | De Vries et al. | |
| 2017/0266153 A1 | 9/2017 | Levy et al. | |
| 2019/0030101 A1 | 1/2019 | Cooper et al. | |
| 2019/0090527 A1 | 3/2019 | Levy | |

FOREIGN PATENT DOCUMENTS

| | | |
|---|---|---|
| WO | WO 2008/024408 | 2/2008 |
| WO | WO 2011/135591 | 11/2011 |
| WO | WO 2014/100231 | 6/2014 |
| WO | WO 2015/068052 | 5/2015 |
| WO | WO 2015/200049 | 12/2015 |
| WO | WO 2016/109624 | 7/2016 |

OTHER PUBLICATIONS

Klauke et al., "The cannabinoid CB2 receptor-selective phytocannabinoid beta-cryophyliene exerts analgesic effects in mouse models of inflammatory and neuropathic pain," European Neuropsychopharmacology, vol. 24, 2014, pp. 608-620.

Maione et al., "Non-psychoactive cannabinoids modulate the descending pathway of antinociception in anaesthetized rats through several mechanisms of action," British Journal of Pharmacology, vol. 162, 2011, pp. 584-596.

Marriot et al., "Pharmaceutical Compounding and Dispensing, 2nd Edition," Pharmaceutical Press, 2010, 305 pages.

McPartland et al., "Cannabis and Cannabis Extracts: Greater than the Sum of Their Parts?," The Haworth Press, Inc., 2001, pp. 103-132.

McPartland et al., "Side Effects of Pharmaceuticals Not Elicited by the Comparable Herbal Medicines: The Case of Tetrahydrocannabinol and Marijuana," Alternative Therapies in Health and Medicine, vol. 5, No. 4, Jul. 1999, pp. 57-62.

Mosely, "Ebbu Announces Groundbreaking Production Scale Purification Process," Business Wire, Jun. 13, 2016. retrieved from www.businesswire.com/news/home/20160613006490/en/Ebbu-Announces-Groundbreaking-Production-Scale-Purification-Process, 2 pages.

Omar et al., "Optimisation and characterisation of marihuana extracts obtained by supercritical fluid extraction and focused ultrasound extraction and retention time locking GC-MS," Journal of Separate Science, vol. 36, 2013, pp. 1397-1404.

Ross et al., "The Volatile Oil Composition of Fresh and Air-Dried Buds of Cannabis sativa," Journal of Natural Products, vol. 59, No. 1, Jan. 1996, pp. 49-51.

Russo et al., "Taming THC: potential cannabis synergy and phytocannabinoid-terpenoid entourage effects," British Journal of Pharmacology, vol. 183, 2011, pp. 1344-1364.

Tomic et al., "Antihyperalgesic and Antiedematous Activities of Bisabolol-Oxides-Rich Matricaria Oil in a Rat Model of Inflammation," Phytotherapy Research, vol. 28, 2014, pp. 759-766.

Wirth et al., "Anti-Inflammatory Properties of Cannabichromene," Life Sciences, vol. 26, No. 23, 1980, 5 pages.

Wright et al., "Cannabinoid CB2 receptors in the gastrointestinal tract: a regulatory system in states of inflammation," British Journal of Pharmacology, vol. 153, 2008, pp. 263-270.

* cited by examiner

WATER SOLUBLE COMPOSITIONS COMPRISING PURIFIED CANNABINOIDS

CROSS-REFERENCE TO RELATED APPLICATIONS

This application is a national stage application under 35 U.S.C. 371 and claims the benefit of PCT Application No. PCT/US2017/049219 having an international filing date of 29 Aug. 2017, which designated the United States, which PCT application claimed the benefit of U.S. Provisional Patent Application Ser. No. 62/380,954, filed on Aug. 29, 2016, the entire disclosures of each of which are incorporated herein by reference.

TECHNICAL FIELD

This disclosure relates to the *cannabis* industry. In particular, this disclosure relates to water soluble cannabinoid formulations, including methods for creating said water soluble cannabinoid formulations.

BACKGROUND

The word "*cannabis*" refers to a genus of flowering plants. Plants of genus *cannabis* include several species, including *Cannabis sativa, Cannabis indica*, and *Cannabis ruderalis*. There is a long history of cultivating plants of genus *cannabis* for hemp fibers, seeds and seed oils, medicinal purposes, and recreational activities.

According to some accounts, cannabis is composed of at least 483 known chemical compounds, which include cannabinoids, terpenoids, flavonoids, nitrogenous compounds, amino acids, proteins, glycoproteins, enzymes, sugars and related compounds, hydrocarbons, alcohols, aldehydes, ketones, acids, fatty acids, esters, lactones, steroids, terpenes, non-cannabinoid phenols, vitamins, and pigments.

Cannabinoids are of particular interest for research and commercialization. Most extractions of cannabis plant matter aim to extract cannabinoids, particularly tetrahydrocannabinol (THC). THC is useful for relieving pain, treating glaucoma, and relieving nausea. THC is also gaining immense popularity as a recreational drug substance. Usually, cannabinoids are extracted from the cannabis plant as part of a crude mixture, combined with other chemical compounds found in the cannabis plant.

Current methods of administration cannabinoids fail to take full advantage of cannabinoid properties. For example, burning plant matter and inhaling the vapor does not allow for selection of certain cannabinoids for their certain desired benefit. One can choose a plant with certain known properties, e.g., THC content, but there is still little to no control over selecting individual cannabinoids. Inhaling smoke also leads to many harmful and toxic compounds introduced into the body.

There exists a need for new cannabinoid formulations. In particular, there exists a need for water soluble cannabinoid formulations. Additionally, there exists a need for methods for producing aqueous cannabinoid formulations. Furthermore, there exists a need for making formulations with increased permeability into the bloodstream. Also, there also exists a need for cannabis formulations which provide increased bioavailability of cannabinoids.

DETAILED DESCRIPTION

Disclosed herein are new cannabinoid formulations, including water soluble cannabinoid formulations. In one embodiment, the formulations disclosed herein are used for creating other new formulations. In one embodiment, the formulations disclosed herein are soluble in other liquids, e.g., aqueous liquids such as juices, soft drinks, wine, cocktails, medicinal preations, coffee, tea, etc.

Disclosed herein are methods of making formulations with increased permeability into the bloodstream. Also disclosed herein are cannabis formulations, which provide increased bioavailability of cannabinoids.

Disclosed herein is a new composition comprising a first purified cannabinoid and Vitamin E TPGS.

As used herein, the term "purified" means extracted, isolated, and/or separated from other compounds, formulations, compositions, matter, and/or mass. In one embodiment, the term "purified" refers to a cannabinoid that is separated from the plant matter from which it was derived. In one embodiment, the term "purified" refers to a cannabinoid (a "purified cannabinoid") that is separated from other cannabinoids that were present in the plant matter from which it was derived. In one embodiment, the term "purified" refers to a cannabinoid (a "purified cannabinoid") that is separated from terpenes that were present in the plant matter from which it was derived. In one embodiment, the term "purified" refers to a cannabinoid (a "purified cannabinoid") that is separated from secondary compounds that were present in the plant matter from which it was derived. In one embodiment, the term "purified" refers to a cannabinoid (a "purified cannabinoid") that is separated from all material that was present in the plant matter from which it was derived.

In one embodiment, the term "purified" refers to a terpene (a "purified terpene") that is separated from other cannabinoids that were present in the plant matter from which it was derived. In one embodiment, the term "purified" refers to a terpene (a "purified terpene") that is separated from terpenes that were present in the plant matter from which it was derived. In one embodiment, the term "purified" refers to a terpene (a "purified terpene") that is separated from secondary compounds that were present in the plant matter from which it was derived. In one embodiment, the term "purified" refers to a terpene (a "purified terpene") that is separated from all material that was present in the plant matter from which it was derived.

Within the context of this disclosure, purified compounds may be purposely formulated with other compounds at various levels of purity. For example, depending on the desired outcome, a particular cannabinoid and/or terpene may be formulated with other molecules when it is 60-65% pure, 65-70% pure, 70-75% pure, 75-80% pure, 80-85% pure, 85-90% pure, 90-95% pure, 95-99% pure, 99-99.9% pure, 99.9+%, or greater than 99% pure. Provided that the ingredients used for purposeful formulation are purified prior to the said purposeful formulation, the act of subsequently formulating them does render them not "purified" within the context of an ingredient list.

As used herein, the term "cannabinoid" refers to a compound belonging to a class of secondary compounds commonly found in plants of genus *cannabis*. In one embodiment, the cannabinoid is found in a plant, e.g., a plant of genus *cannabis*, and is sometimes referred to as a phytocannabinoid. In one embodiment, the cannabinoid is found in a mammal, sometimes called a endocannabinoid. In one embodiment, the cannabinoid is made in a laboratory setting, sometimes called a synthetic cannabinoid. In one embodiment, the cannabinoid acts upon a cellular receptor, such as a G-coupled protein receptor (e.g., a serotonin receptor, a cannabinoid receptor, TRPV1, an opioid receptor, etc.) thereby causing a response on the brain or body. In one embodiment, the cannabinoid affects the activity of other compounds at one or more receptors by acting as an agonist, partial agonist, inverse agonist, antagonist, etc.

In many cases, a cannabinoid can be identified because its chemical name will include the text string "*cannabi* in the name.

Within the context of this application, where reference is made to a particular cannabinoid, each of the acid and/or decarboxylated forms are contemplated as both single molecules and mixtures.

Examples of cannabinoids include, but are not limited to, Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-$C_4$ (CBD-$C_4$), Cannabidivarinic Acid (CBDVA), Cannabidivarin (CBDV), Cannabidiorcol (CBD-$C_1$), Tetrahydrocannabinolic acid A (THCA-A), Tetrahydrocannabinolic acid B (THCA-B), Tetrahydrocannabinolic Acid (THCA), Tetrahydrocannabinol (THC), Tetrahydrocannabinolic acid $C_4$ (THCA-$C_4$), Tetrahydrocannbinol $C_4$ (THC-$C_4$), Tetrahydrocannabivarinic acid (THCVA), Tetrahydrocannabivarin (THCV), Tetrahydrocannabiorcolic acid (THCA-$C_1$), Tetrahydrocannabiorcol (THC-$C_1$), $\Delta^7$-cis-iso-tetrahydrocannabivarin, $\Delta^8$-tetrahydrocannabinolic acid ($\Delta$8-THCA), Cannabivarinodiolic (CBNDVA), Cannabivarinodiol (CBNDV), $\Delta^8$-tetrahydrocannabinol ($\Delta^8$-THC), $\Delta^9$-tetrahydrocannabinol ($\Delta^9$-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabivarinselsoin (CBEV), Cannabivarinselsoinic Acid (CBEVA), Cannabielsoic Acid (CBEA), Cannabielvarinsoin (CBLV), Cannabielvarinsoinic Acid (CBLVA), Cannabinolic acid (CBNA), Cannabinol (CBN), Cannabivarinic Acid (CBNVA), Cannabinol methylether (CBNM), Cannabinol-$C_4$ (CBN-$C_4$), Cannabivarin (CBV), Cannabino-$C_2$ (CBN-$C_2$), Cannabiorcol (CBN-$C_1$), Cannabinodiol (CBND), Cannabinodiolic Acid (CBNDA), Cannabinodivarin (CBDV), Cannabitriol (CBT), 10-Ethoxy-9-hydroxy-$\Delta^{8a}$-tetrahydrocannabinol, 8,9-Dihydroxy-$\Delta^{6a(10a)}$-tetrahydrocannabinol (8,9-Di-OH-CBT-$C_5$), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-$\Delta^{6a(10a)}$-tetrahydrocannabinol (OTHC), $\Delta^9$-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E,4E,8Z,10Z-tetraenoic acid isobutylamide, and Dodeca-2E,4E-dienoic acid isobutylamide.

In one embodiment, the first purified cannabinoid is chosen from THC, D9-THC, D8-THC, THCA, THCV, D8-THCV, D9-THCV, THCVA, CBD, CBDA, CBDV, CBDVA, CBC, CBCA, CBCV, CBCVA, CBG, CBGA, CBGV, CBGVA, CBN, CBNA, CBNV, CBNVA, CBND, CBNDA, CBNDV, CBNDVA, CBE, CBEA, CBEV, CBEVA, CBL, CBLA, CBLV, or CBLVA.

As used herein, the term "THC" refers to tetrahydrocannabinol and has the following structural formula:

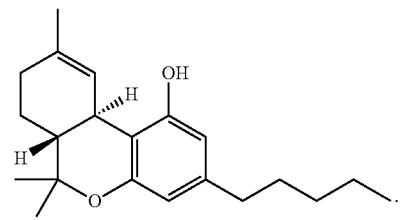 [SMILES: CCCCCc1cc(O)c2c(c1)OC(C)(C)[C@@H]1CCC(C)=C[C@@H]21]

Within the context of this disclosure, compositions comprising THC are formulated with other compounds, thereby providing previously unavailable aqueous formulations.

As used herein, the term "THCA" refers to tetrahydrocannabinolic acid and has the following structural formula:

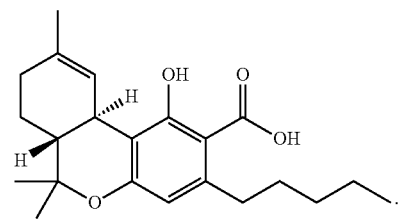 [SMILES: CCCCCc1cc2c(c(O)c1C(=O)O)[C@@H]1C=C(C)CC[C@H]1C(C)(C)O2]

Decarboxylating THCA with heat, light, etc., forms THC, D8-THC, D9-THC, and other potential cannabinoids. Within the context of this disclosure, compositions comprising THCA are formulated with other compounds, thereby providing previously unavailable aqueous formulations.

As used herein, the term "THCV" refers to tetrahydrocannabivarin and has the following structural formula:

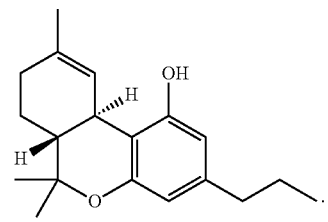 [SMILES: CCCc1cc(O)c2c(c1)OC(C)(C)[C@@H]1CCC(C)=C[C@@H]21]

Within the context of this disclosure, compositions comprising THCV are formulated with other compounds, thereby providing previously unavailable aqueous formulations.

As used herein, the term "THCVA" refers to tetrahydrocannabivarinic acid and has the following structural formula:

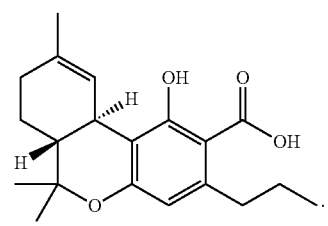 [SMILES: CCCc1cc2c(c(O)c1C(=O)O)[C@@H]1C=C(C)CC[C@H]1C(C)(C)O2]

Decarboxylating THCVA with heat, light, etc., forms THCV, D8-THCV, D9-THCV, and other possible cannabinoid derivatives. Within the context of this disclosure, compositions comprising THCVA are formulated with other compounds, thereby providing previously unavailable aqueous formulations.

As used herein, the term "D8-THC" refers to delta-8-tetrahydrocannabinol and has the following structural formula:

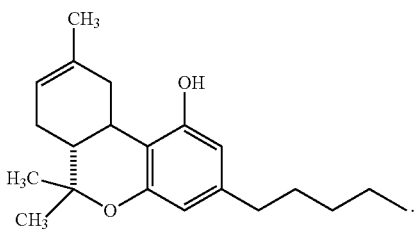

Within the context of this disclosure, compositions comprising D8-THC are formulated with other compounds, thereby providing previously unavailable aqueous formulations.

As used herein, the term "D8-THCV" refers to delta-8-tetrahydrocannabivarin and has the following structural formula:

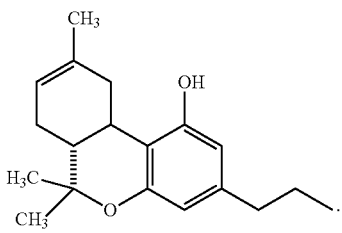

Within the context of this disclosure, compositions comprising D8-THCV are formulated with other compounds, thereby providing previously unavailable aqueous formulations.

As used herein, the term "D9-THC" refers to delta-9-tetrahydrocannabinol and has the following structural formula:

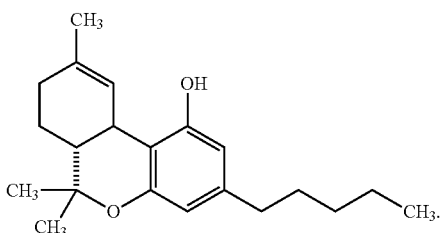

Within the context of this disclosure, compositions comprising D9-THC are formulated with other compounds, thereby providing previously unavailable aqueous formulations.

As used herein, the term "D9-THCV" refers to delta-9-tetrahydrocannabivarin and has the following structural formula:

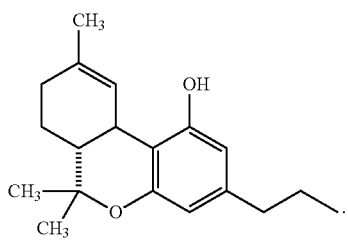

Within the context of this disclosure, compositions comprising D9-THCV are formulated with other compounds, thereby providing previously unavailable aqueous formulations.

As used herein, the term "CBD" refers to cannabidiol and has the following structural formula:

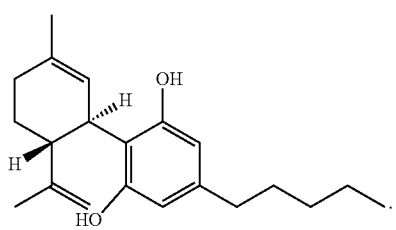 [SMILES: C=C(C)[C@@H]1CCC(C)=C[C@H]1c1c(O)cc(CCCCC)cc1O]

Within the context of this disclosure, compositions comprising CBD are formulated with other compounds, thereby providing previously unavailable aqueous formulations.

As used herein, the term "CBDA" refers to cannabidiolic acid and has the following structural formula:

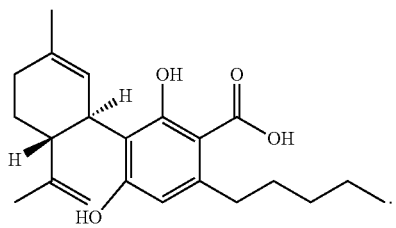 [SMILES: C=C(C)[C@@H]1CCC(C)=C[C@H]1c1c(O)cc(CCCCC)c(C(=O)O)c1O]

Decarboxylating CBDA with heat, light, etc., forms CBD and other possible cannabinoid derivatives. Within the context of this disclosure, compositions comprising CBDA are formulated with other compounds, thereby providing previously unavailable aqueous formulations.

As used herein, the term "CBDV" refers to cannabidivarin and has the following structural formula:

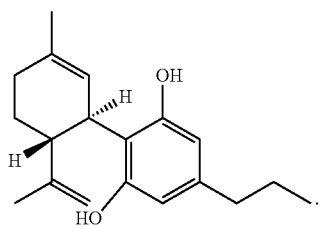 [SMILES: C=C(C)[C@@H]1CCC(C)=C[C@H]1c1c(O)cc(CCC)cc1O]

Within the context of this disclosure, compositions comprising CBDV are formulated with other compounds, thereby providing previously unavailable aqueous formulations.

As used herein, the term "CBDVA" refers to cannabidivarinic acid and has the following structural formula:

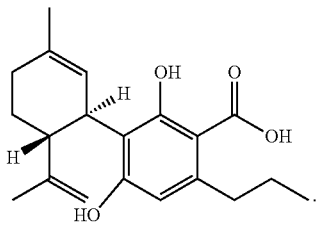 [SMILES: C=C(C)[C@@H]1CCC(C)=C[C@H]1c1c(O)cc(CCC)c(C(=O)O)c1O]

Decarboxylating CBDVA with heat, light, etc., forms CBDV and other possible cannabinoid derivatives. Within the context of this disclosure, compositions comprising CBDVA are formulated with other compounds, thereby providing previously unavailable aqueous formulations.

As used herein, the term "CBC" refers to cannabichromene and has the following structural formula:

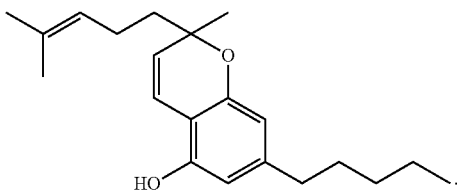 [SMILES: CCCCCc1cc(O)c2c(c1)OC(C)(CCC=C(C)C)C=C2]

Within the context of this disclosure, compositions comprising CBC are formulated with other compounds, thereby providing previously unavailable aqueous formulations.

As used herein, the term "CBCA" refers to cannabichromenic acid and has the following structural formula:

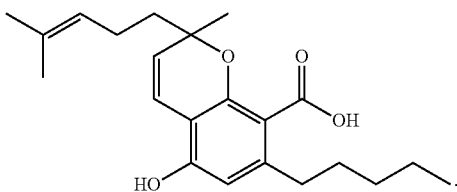 [SMILES: CCCCCc1cc(O)c2c(c1C(=O)O)OC(C)(CCC=C(C)C)C=C2]

Decarboxylating CBCA with heat, light, etc., forms CBC and other possible cannabinoid derivatives. Within the context of this disclosure, compositions comprising CBCA are formulated with other compounds, thereby providing previously unavailable aqueous formulations.

As used herein, the term "CBCV" refers to cannabichromevarin and has the following structural formula:

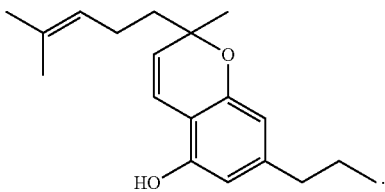 [SMILES: CCCc1cc(O)c2c(c1)OC(C)(CCC=C(C)C)C=C2]

Within the context of this disclosure, compositions comprising CBCV are formulated with other compounds, thereby providing previously unavailable aqueous formulations.

As used herein, the term "CBCVA" refers to cannabichromevarinic acid and has the following structural formula:

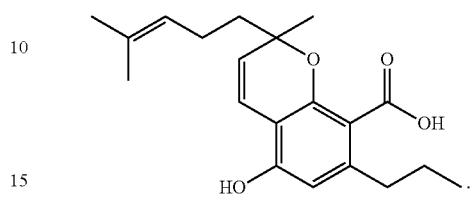

Decarboxylating CBCVA with heat, light, etc., forms CBCV and other possible cannabinoid derivatives. Within the context of this disclosure, compositions comprising CBCVA are formulated with other compounds, thereby providing previously unavailable aqueous formulations.

As used herein, the term "CBG" refers to cannabigerol and has the following structural formula:

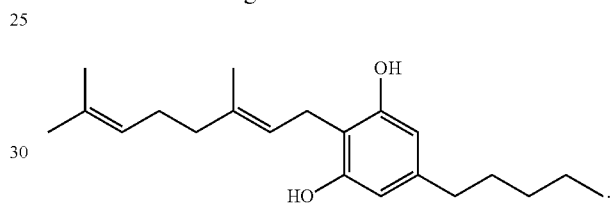

Within the context of this disclosure, compositions comprising CBG are formulated with other compounds, thereby providing previously unavailable aqueous formulations.

As used herein, the term "CBGA" refers to cannabigerolic acid and has the following structural formula:

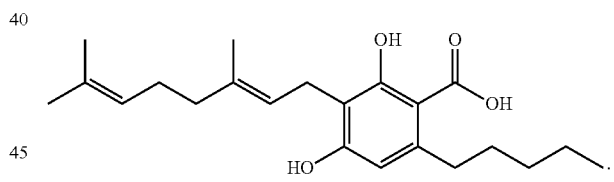

Decarboxylating CBGA with heat, light, etc., forms CBG and other possible cannabinoid derivatives. Within the context of this disclosure, compositions comprising CBGA are formulated with other compounds, thereby providing previously unavailable aqueous formulations.

As used herein, the term "CBGV" refers to cannabigerovarin and has the following structural formula:

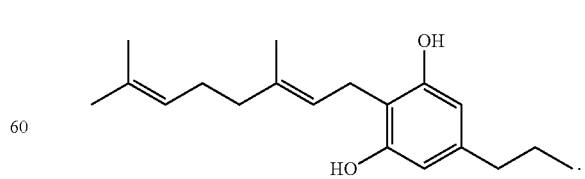

Within the context of this disclosure, compositions comprising CBGV are formulated with other compounds, thereby providing previously unavailable aqueous formulations.

As used herein, the term "CBGVA" refers to cannabigerovarinic acid and has the following structural formula:

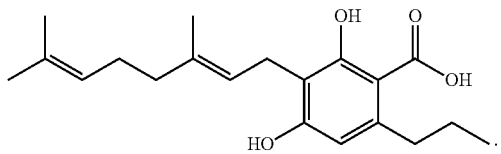 [SMILES: CCCc1cc(O)c(C/C=C(\C)CCC=C(C)C)c(O)c1C(=O)O]

Decarboxylating CBGVA with heat, light, etc., forms CBGV and other possible cannabinoid derivatives. Within the context of this disclosure, compositions comprising CBGVA are formulated with other compounds, thereby providing previously unavailable aqueous formulations.

As used herein, the term "CBN" refers to cannabinol and has the following structural formula:

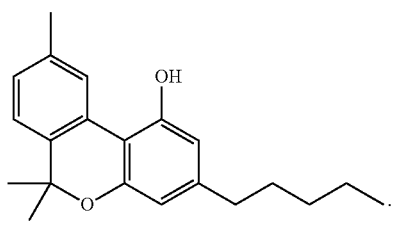 [SMILES: CCCCCc1cc(O)c2c(c1)OC(C)(C)c1ccc(C)cc1-2]

Within the context of this disclosure, compositions comprising CBN are formulated with other compounds, thereby providing previously unavailable aqueous formulations.

As used herein, the term "CBNA" refers to cannabinolic acid and has the following structural formula:

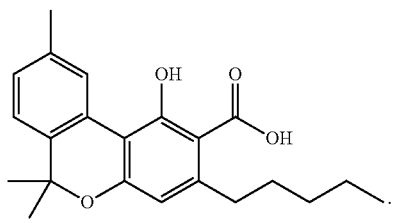 [SMILES: CCCCCc1cc2c(c(O)c1C(=O)O)-c1cc(C)ccc1C(C)(C)O2]

Decarboxylating CBNA with heat, light, etc., forms CBN and other possible cannabinoid derivatives. Within the context of this disclosure, compositions comprising CBNA are formulated with other compounds, thereby providing previously unavailable aqueous formulations.

As used herein, the term "CBNV" or "CBV" refers to cannabivarin and has the following structural formula:

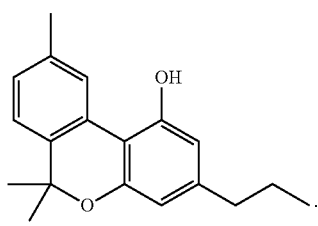 [SMILES: CCCc1cc(O)c2c(c1)OC(C)(C)c1ccc(C)cc1-2]

Within the context of this disclosure, compositions comprising CBNV are formulated with other compounds, thereby providing previously unavailable aqueous formulations.

As used herein, the term "CBNVA" refers to cannabivarinic acid and has the following structural formula:

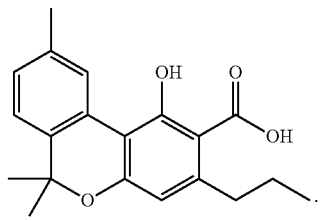 [SMILES: CCCc1cc2c(c(O)c1C(=O)O)-c1cc(C)ccc1C(C)(C)O2]

Decarboxylating CBNVA with heat, light, etc., forms CBNV and other possible cannabinoid derivatives. Within the context of this disclosure, compositions comprising CBNVA are formulated with other compounds, thereby providing previously unavailable aqueous formulations.

As used herein, the term "CBND" refers to cannabinodiol and has the following structural formula:

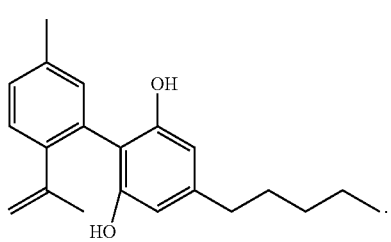 [SMILES: C=C(C)c1ccc(C)cc1-c1c(O)cc(CCCCC)cc1O]

Within the context of this disclosure, compositions comprising CBND are formulated with other compounds, thereby providing previously unavailable aqueous formulations.

As used herein, the term "CBNDA" refers to cannabinodiolic acid and has the following structural formula:

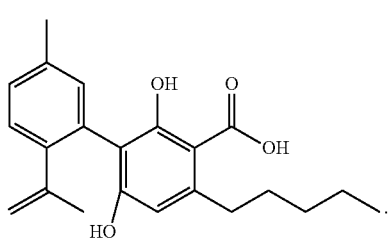 [SMILES: C=C(C)c1ccc(C)cc1-c1c(O)cc(CCCCC)c(C(=O)O)c1O]

Decarboxylating CBNDA with heat, light, etc., forms CBND and other possible cannabinoid derivatives. Within the context of this disclosure, compositions comprising CBNDA are formulated with other compounds, thereby providing previously unavailable aqueous formulations.

As used herein, the term "CBNDV" refers to cannabivarinodiol and has the following structural formula:

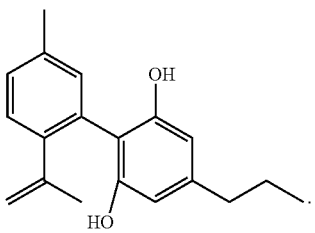 [SMILES: C=C(C)c1ccc(C)cc1-c1c(O)cc(CCC)cc1O]

Within the context of this disclosure, compositions comprising CBNDV are formulated with other compounds, thereby providing previously unavailable aqueous formulations.

As used herein, the term "CBNDVA" refers to cannabivarinodiolic acid and has the following structural formula:

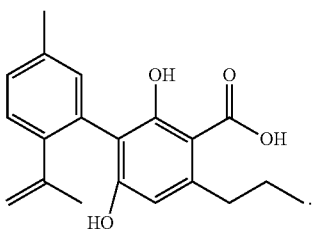 [SMILES: C=C(C)c1ccc(C)cc1-c1c(O)cc(CCC)c(C(=O)O)c1O]

Decarboxylating CBNDVA with heat, light, etc., forms CBNDV and other possible cannabinoid derivatives. Within the context of this disclosure, compositions comprising CBNDVA are formulated with other compounds, thereby providing previously unavailable aqueous formulations.

As used herein, the term "CBL" refers to cannabicyclol and has the following structural formula:

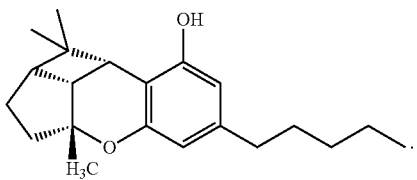

Within the context of this disclosure, compositions comprising CBL are formulated with other compounds, thereby providing previously unavailable aqueous formulations.

As used herein, the term "CBLA" refers to cannabicyclolic acid and has the following structural formula:

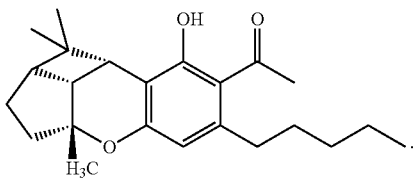

Decarboxylating CBLA with heat, light, etc., forms CBL and other possible cannabinoid derivatives. Within the context of this disclosure, compositions comprising CBLA are formulated with other compounds, thereby providing previously unavailable aqueous formulations.

As used herein, the term "CBLV" refers to cannabicyclovarin and has the following structural formula:

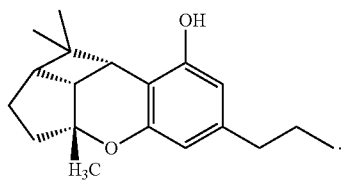

Within the context of this disclosure, compositions comprising CBLV are formulated with other compounds, thereby providing previously unavailable aqueous formulations.

As used herein, the term "CBLVA" refers to cannabielvarinsoinic acid and has the following structural formula:

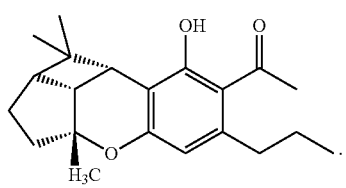

Decarboxylating CBLVA with heat, light, etc., forms CBLV and other possible cannabinoid derivatives. Within the context of this disclosure, compositions comprising CBLVA are formulated with other compounds, thereby providing previously unavailable aqueous formulations.

As used herein, the term "CBE" refers to cannabielsoin and has the following structural formula:

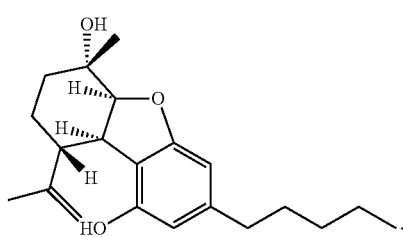

Within the context of this disclosure, compositions comprising CBE are formulated with other compounds, thereby providing previously unavailable aqueous formulations.

As used herein, the term "CBEA" refers to cannabielsoic acid and has the following structural formula:

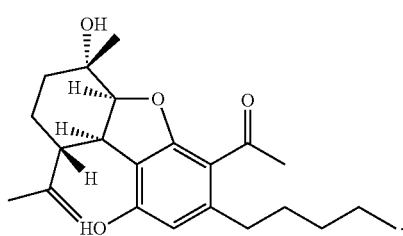

Decarboxylating CBEA with heat, light, etc., forms CBE and other possible cannabinoid derivatives. Within the context of this disclosure, compositions comprising CBEA are formulated with other compounds, thereby providing previously unavailable aqueous formulations.

As used herein, the term "CBEV" refers to cannabivarinselsoin and has the following structural formula:

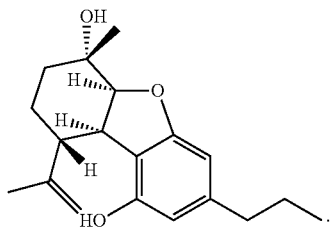

Within the context of this disclosure, compositions comprising CBEV are formulated with other compounds, thereby providing previously unavailable aqueous formulations.

As used herein, the term "CBEVA" refers to cannabivarinselsoinic acid and has the following structural formula:

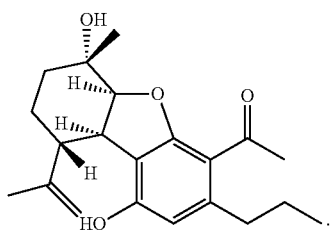

Decarboxylating CBEVA with heat, light, etc., forms CBEV and other possible cannabinoid derivatives. Within the context of this disclosure, compositions comprising CBEVA are formulated with other compounds, thereby providing previously unavailable aqueous formulations.

As used herein, the term "Vitamin E TPGS" refers to the esterification of Vitamin E succinate with polyethylene glycol 1000 resulting in the following structural formula:

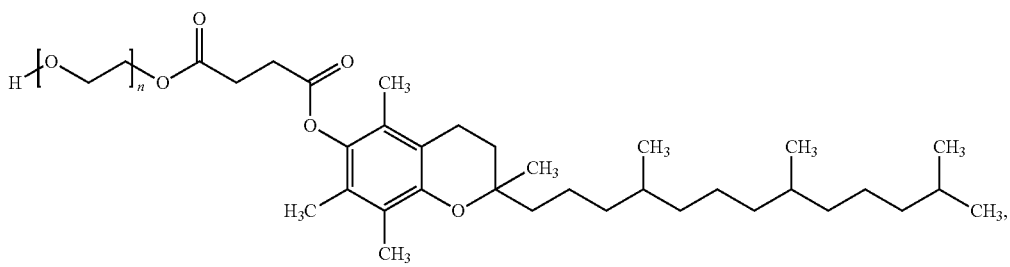

where "n" is an integer.

Within the context of this disclosure, Vitamin E TPGS is formulated with a compound or compounds found in a plant of genus *cannabis* to increase the solubility and bioavailability of poorly water soluble lipophilic compounds.

In one embodiment, the compositions disclosed herein comprise a ratio of Vitamin E TPGS to the first purified cannabinoid of about 90:10 to about 70:30 by percent mass.

In one embodiment, the compositions disclosed herein comprise a ratio of Vitamin E TPGS to the first purified cannabinoid of about 85:15 to about 75:25 by percent mass.

In one embodiment, the compositions disclosed herein comprise a ratio of Vitamin E TPGS to the first purified cannabinoid of about 82:18 to about 78:22 by percent mass.

In one embodiment, the compositions disclosed herein comprise a ratio of Vitamin E TPGS to the first purified cannabinoid of about 80:20 to about 70:30 by percent mass.

In one embodiment, the compositions disclosed herein comprise a ratio of Vitamin E TPGS to the first purified cannabinoid of about 90:10 to about 80:20 by percent mass.

As used herein, the term "percent mass" refers to the amount of matter of a compound expressed as a fraction of 100. In one embodiment, the percent mass is expressed in grams. In one embodiment, the percent mass is expressed in ounces. In one embodiment, the percent mass is expressed in moles. In one embodiment, the percent mass is the amount of a first purified cannabinoid in a composition. In one embodiment, the percent is the amount of Vitamin E TPGS in a composition. In one embodiment, the percent mass is calculated with the following formula:

$$\text{mass of compound} + \text{total mass of sample} \times 100$$

For example:

$$5.0 \text{ g THC} + 100 \text{ g sample} \times 100 = 5\%$$

As used herein, the term "ratio" refers to the relative amount of one or more compounds in relation to another compound or compounds. In one embodiment, the ratio is in reference to the mass of one compound to another. In one embodiment, the ratio is in reference to the mass percent of one compound to another. In one embodiment, the ratio is in reference to the dry weight of one compound to another. In one embodiment, the ratio is in reference to the volume of one compound to another. In one embodiment, the ratio is in reference to the molar mass of one compound to another.

In one embodiment, the ratio is the amount of a first purified cannabinoid to the amount of Vitamin E TPGS. In one embodiment, the ratio is the amount of a first purified cannabinoid and a second purified cannabinoid to the amount of Vitamin E TPGS. In one embodiment, the ratio is the amount of a first purified cannabinoid and a second purified cannabinoid to the amount of Vitamin E TPGS.

In one embodiment, the ratio of the first purified cannabinoid to Vitamin E TPGS is about 1:1 to 1:10.

In one embodiment, the ratio of the first purified cannabinoid to Vitamin E TPGS is about 1:1 to 1:8.

In one embodiment, the ratio of the first purified cannabinoid to Vitamin E TPGS is about 1:1 to 1:6.

In one embodiment, the ratio of the first purified cannabinoid to Vitamin E TPGS is about 1:1 to 1:4.

In one embodiment, the ratio of the first purified cannabinoid to Vitamin E TPGS is about 1:1 to 1:2.

In one embodiment, the compounds disclosed herein comprise a terpene.

In one embodiment, the compounds disclosed herein comprise a purified terpene.

Examples of terpenes within the context of this disclosure include: 7,8-dihydro-alpha-ionone, 7,8-dihydro-beta-ionone, Acetanisole, Acetic Acid, Acetyl Cedrene, Anethole, Anisole, Benzaldehyde, Bergamotene (Alpha-cis-Bergamotene) (Alpha-trans-Bergamotene), Bisabolol (Beta-Bisabolol), Alpha, Bisabolol, Borneol, Bornyl Acetate, Butanoic/ Butyric Acid, Cadinene (Alpha-Cadinene) (Gamma-Cadinene), Cafestol, Caffeic acid, Camphene, Camphor, Capsaicin, Carene (Delta-3-Carene), Carotene, Carvacrol, Dextro-Carvone, Laevo-Carvone, Caryophyllene (Beta-Caryophyllene), Caryophyllene oxide, Cedrene (Alpha-Cedrene) (Beta-Cedrene), Cedrene Epoxide (Alpha-Cedrene Epoxide), Cedrol, Cembrene, Chlorogenic Acid, Cinnamaidehyde, Alpha-amyl-Cinnamaldehyde, Alpha-hexyl-Cinnamaidehyde, Cinnamic Acid, Cinnamyl Alcohol, Citronellal, Citronellol, Cryptone, Curcumene (Alpha-Curcumene) (Gamma-Curcumene), Decanal, Dehydrovomifoliol, Diallyl Disulfide, Dihydroactinidiolide, Dimethyl Disulfide, Eicosane/Icosane, Elemene (Beta-Elemene), Estragole, Ethyl acetate, Ethyl Cinnamate, Ethyl maltol, Eucalyptol/1, 8-Cineole, Eudesmol (Alpha-Eudesmol) (Beta-Eudesmol) (Gamma-Eudesmol), Eugenol, Euphol, Farnesene, Farnesol, Fenchol (Beta-Fenchol), Fenchone, Geraniol, Geranyl acetate, Germacrenes, Germacrene B, Guaia-1(10),11-diene, Guaiacol, Guaiene (Alpha-Guaiene), Gurjunene (Alpha-Gurjunene), Hemiarin, Hexanaldehyde, Hexanoic Acid, Humulene (Alpha-Humulene) (Beta-Humulene), Ionol (3-oxo-alpha-ionol) (Beta-Ionol), Ionone (Alpha-Ionone) (Beta-Ionone), Ipsdienol, Isoamyl Acetate, Isoamyl Alcohol, Isoamyl Formate, Isoborneol, Isomyrcenol, Isopulegol, Isovaleric Acid, Isoprene, Kahweol, Lavandulol, Limonene, Gamma-Linolenic Acid, Linalool, Longifolene, Alpha-Longipinene, Lycopene, Menthol, Methyl butyrate, 3-Mercapto-2-Methylpentanal, Mercaptan/Thiols, Beta-Mercaptoethanol, Mercaptoacetic Acid, Allyl Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (Beta-Myrcene), Gamma-Muurolene, Nepetalactone, Nerol, Nerolidol, Neryl acetate, Nonanaldehyde, Nonanoic Acid, Ocimene, Octanal, Octanoic Acid, P-Cymene, Pentyl butyrate, Phellandrene, Phenylacetaldehyde, Phenylethanethiol, Phenylacetic Acid, Phytol, Pinene, Beta-Pinene, Propanethiol, Pristimerin, Pulegone, Quercetin, Retinol, Rutin, Sabinene, Sabinene Hydrate, cis-Sabinene Hydrate, trans-Sabinene Hydrate, Safranal, Alpha-Selinene, Alpha-Sinensal, Beta-Sinensal, Beta-Sitosterol, Squalene, Taxadiene, Terpin hydrate, Terpineol, Terpine-4-ol, Alpha-Terpinene, Gamma-Terpinene, Terpinolene, Thiophenol, Thujone, Thymol, Alpha-Tocopherol, Tonka Undecanone, Undecanal, Valeraldehyde/Pentanal, Verdoxan, Alpha-Ylangene, Umbelliferone, or Vanillin.

Within the context of this disclosure, the term terpene includes the α-(alpha), β-(beta), γ-(gamma), oxo-, isomers, or any combinations thereof.

In one embodiment, the purified terpene is chosen from Limonene, Nerolidol, Beta-Myrcene, Linalool, Alpha-Caryophyllene, Beta-Caryophyllene, Alpha-Pinene, Beta-Pinene, Alpha-Bisabolol, Delta-3-Carene, Borneol, p-Cymene, Eucalyptol, Alpha-Humulene, Alpha-Terpineol, Terpinolene, Pulegone, Camphene, or Geraniol.

In one embodiment, the purified cannabinoid is contained within a micelle of Vitamin E TPGS.

As used herein, the term "micelle" refers to a collection of molecules arranged alongside one another in a spherical form often having a pocket inside. In one embodiment, the micelle comprises a lipid molecule. In one embodiment, the lipid molecule comprises both a hydrophobic and hydrophilic region. In one embodiment, the micelle is in a solvent. In one embodiment, the hydrophilic region is in contact with surrounding solvent, sequestering the hydrophobic region in the micelle centre. In one embodiment, the micelle is in water and the polar group is on the outside and a hydrophobic end sequesters inside the spherical shape. In one embodiment, the micelle is a reverse micelle, i.e., the hydrophilic region of a molecule is surrounded by a nonpolar solvent resulting in a water in oil system. In one embodiment, the reverse micelle comprises hydrophobic groups extended away from the center while hydrophilic groups are sequestered inside the spherical shape.

As used herein, the term "contained within" refers to molecules, e.g. cannabinoids and/or terpenes, that are sequestered inside a spherical shape formed by micelles and reverse micelles. In one embodiment, a cannabinoid contained within a micelle allows said cannabinoid to disperse or dissolve within an aqueous formulation.

Disclosed herein, is a method of making an aqueous cannabinoid formulation comprising adding 0-3% water, by mass percent, to a composition comprising a first purified cannabinoid and Vitamin E TPGS.

As used herein, the term "aqueous cannabinoid formulation" refers to a solution wherein a first purified cannabinoid and Vitamin E TPGS are dispersed throughout water and wherein the water acts as a solvent. In one embodiment, the aqueous cannabind formulation is made by methods disclosed herein. In one embodiment, the aqueous cannabinoid formulation comprises a second purified cannabinoid. In one embodiment, the aqueous cannabinoid formulation comprises a third purified cannabinoid. In one embodiment, the aqueous cannabinoid formulation comprises a first purified terpene. In one embodiment, the aqueous cannabinoid formulation comprises a second purified terpene.

In one embodiment, water accounts for between 0-10% of the mass percent of the aqueous cannabinoid formulation.

In one embodiment, water accounts for between 0-5% of the mass percent of the aqueous cannabinoid formulation.

In one embodiment, water accounts for between 0-3% of the mass percent of the aqueous cannabinoid formulation.

In one embodiment, water accounts for between 0-1% of the mass percent of the aqueous cannabinoid formulation.

In one embodiment, the first purified cannabinoid is THC.

In one embodiment, the aqueous cannabinoid formulations disclosed herein comprise 50 to 99.9% THC by percent mass.

In one embodiment, the first purified cannabinoid is THCA.

In one embodiment, the aqueous cannabinoid formulations disclosed herein comprise 50 to 99.9% THCA by percent mass.

In one embodiment, the first purified cannabinoid is THCV.

In one embodiment, the aqueous cannabinoid formulations disclosed herein comprise 50 to 99.9% THCV by percent mass.

In one embodiment, the first purified cannabinoid is THCVA.

In one embodiment, the aqueous cannabinoid formulations disclosed herein comprise 50 to 99.9% THCVA by percent mass.

In one embodiment, the first purified cannabinoid is CBC.

In one embodiment, the aqueous cannabinoid formulations disclosed herein comprise 50 to 99.9% CBC by percent mass.

In one embodiment, the first purified cannabinoid is CBCA.

In one embodiment, the aqueous cannabinoid formulations disclosed herein comprise 50 to 99.9% CBCA by percent mass.

In one embodiment, the first purified cannabinoid is CBCV.

In one embodiment, the aqueous cannabinoid formulations disclosed herein comprise 50 to 99.9% CBCV by percent mass.

In one embodiment, the first purified cannabinoid is CBCVA.

In one embodiment, the aqueous cannabinoid formulations disclosed herein comprise 50 to 99.9% CBCVA by percent mass.

In one embodiment, the first purified cannabinoid is CBD.

In one embodiment, the aqueous cannabinoid formulations disclosed herein comprise 50 to 99.9% CBD by percent mass.

In one embodiment, the first purified cannabinoid is CBDA.

In one embodiment, the aqueous cannabinoid formulations disclosed herein comprise 50 to 99.9% CBDA by percent mass.

In one embodiment, the first purified cannabinoid is CBDV.

In one embodiment, the aqueous cannabinoid formulations disclosed herein comprise 50 to 99.9% CBDV by percent mass.

In one embodiment, the first purified cannabinoid is CBDVA.

In one embodiment, the aqueous cannabinoid formulations disclosed herein comprise 50 to 99.9% CBDVA by percent mass.

In one embodiment, the first purified cannabinoid is CBG.

In one embodiment, the aqueous cannabinoid formulations disclosed herein comprise 50 to 99.9% CBG by percent mass.

In one embodiment, the first purified cannabinoid is CBGA.

In one embodiment, the aqueous cannabinoid formulations disclosed herein comprise 50 to 99.9% CBGA by percent mass.

In one embodiment, the first purified cannabinoid is CBGV.

In one embodiment, the aqueous cannabinoid formulations disclosed herein comprise 50 to 99.9% CBGV by percent mass.

In one embodiment, the first purified cannabinoid is CBGVA.

In one embodiment, the aqueous cannabinoid formulations disclosed herein comprise 50 to 99.9% CBGVA by percent mass.

As used herein, the term "water soluble" refers to a compound or compounds dissolvable in water or liquid. In one embodiment, water soluble comprises dissolving a compound in water. In one embodiment, dissolving comprises heating. In one embodiment, dissolving comprises stirring. In one embodiment, dissolving comprises shaking. In one embodiment, dissolving comprises mixing. In one embodiment, a powder is water soluble. In one embodiment, a first purified cannabinoid composition is water soluble.

In one embodiment, the compositions disclosed herein comprise a second purified cannabinoid. In one embodiment, the compositions disclosed herein comprise a third purified cannabinoid. In one embodiment, the compositions disclosed herein comprise more than three purified cannabinoids. In one embodiment, the compositions disclosed herein comprises a total purified cannabinoid content.

As used herein, the term "total purified cannabinoid content" refers to the entire amount of identifiable cannabinoids within a composition. In one embodiment, the total purified cannabinoid content is measured by grams. In one embodiment, the total purified cannabinoid content is measured by volume. In one embodiment, the total purified cannabinoid content is measured by moles. In one embodiment, the total purified cannabinoid content is measured by mass percent. In one embodiment, the total purified cannabinoid content is determined by chromatography, e.g., HPLC. In one embodiment, the total purified cannabinoid content comprises terpenes.

In one embodiment, the compositions disclosed herein comprise a ratio of Vitamin E TPGS to total purified cannabinoid content of about 90:10 to about 70:30 by mass.

In one embodiment, the compositions disclosed herein comprise a ratio of Vitamin E TPGS to total purified cannabinoid content of about 85:15 to about 75:25 by mass.

In one embodiment, the compositions disclosed herein comprise a ratio of Vitamin E TPGS to total purified cannabinoid content of about 82:18 to about 78:22 by mass.

In one embodiment, the compositions disclosed herein comprise a ratio of Vitamin E TPGS to total purified cannabinoid content of about 80:20 to about 70:30 by mass.

In one embodiment, the compositions disclosed herein comprise a ratio of Vitamin E TPGS to total purified cannabinoid content of about 90:10 to about 80:20 by mass.

In one embodiment, the ratio of the total purified cannabinoid content to Vitamin E TPGS is about 1:1 to 1:10.

In one embodiment, the ratio of the total purified cannabinoid content to Vitamin E TPGS is about 1:1 to 1:8.

In one embodiment, the ratio of the total purified cannabinoid content to Vitamin E TPGS is about 1:1 to 1:6.

In one embodiment, the ratio of the total purified cannabinoid content to Vitamin E TPGS is about 1:1 to 1:4.

In one embodiment, the ratio of the total purified cannabinoid content to Vitamin E TPGS is about 1:1 to 1:2.

In one embodiment, the composition disclosed herein is in the form of a tablet.

As used herein, the term "tablet" refers to a dry solid. In one embodiment, the tablet is composed of active ingredients, e.g., a first purified cannabinoid. In one embodiment, the tablet is in dry form. In one embodiment, the tablet is made by molding or compressing a powder. In one example, the tablet is made by compressing a dry powder of the active ingredients and a filler (e.g., an excipient) forming a pill shape. In one embodiment, the tablet is a dosage of an active ingredient. In one embodiment, the dosage is determined by the active ingredient(s), e.g., a first purified cannabinoid. In one embodiment, the tablet comprises an effervescent.

In one embodiment, the composition disclosed herein comprises an alcohol.

In one embodiment, the composition disclosed herein comprises ethanol.

As used herein, the term "ethanol" refers to a compound with the following structural formula:

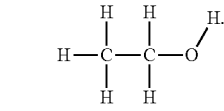

Ethanol is a volatile, flammable, colorless liquid with a slight chemical odor. Ethanol is often used as an antiseptic, a solvent, a fuel, and an active fluid in thermometers because of its low freezing point. Ethanol is also present in some tinctures and alcoholic beverages.

In one embodiment, the compositions disclosed herein comprise a sugar.

As used herein, the term "sugar" refers to a compound used by organisms to store energy. Sugar is often used in food products as a sweetener and may provide other benefits, e.g., preservative, texture modifier, flavoring agent, bulking agent, etc. In one embodiment, the sugar is a carbohydrate. In one embodiment, the sugar is a monosaccharide. In one embodiment, the sugar is a disaccharide. In one embodiment, the sugar is a oligosaccharide. In one embodiment, the sugar is a short composed of carbon, hydrogen, and oxygen. In one embodiment, the sugar has the formula $C_nH_{2n}O_n$, wherein n is an integer. In one embodiment, n is 3. In one embodiment, n is 4. In one embodiment, n is 5. In one embodiment, n is 6. In one embodiment, n is 7.

Within the context of this disclosure, the term sugar may also refer to a number of naturally occurring or synthetic compounds imparting sweetness. For example, maltodextrin, sorbitol, stevia, mannitol, aspartame, sucralose, isomalt, xylitol, etc.

In one embodiment, the sugar is fructose. In one embodiment, the sugar is sucrose. In one embodiment, the compositions disclosed herein comprise more than one sugar. In one embodiment, the compositions disclosed herein comprise sucrose and fructose.

Disclosed herein is a new method of making a water soluble composition having a first purified cannabinoid, comprising:
 separating a first purified cannabinoid from cannabis plant material;
 adding the first purified cannabinoid to Vitamin E TPGS to create a mixture of Vitamin E TPGS and the first purified cannabinoid;
 heating said mixture to a first temperature;
 adding water to the mixture of Vitamin E TPGS and the first purified cannabinoid to create an aqueous cannabinoid formulation comprising the mixture of Vitamin E TPGS and the first purified cannabinoid; and
 cooling the aqueous formulation to a second temperature.

As used herein, the term "separating a first cannabinoid from cannabis plant material" refers to isolating a cannabinoid from the rest of the plant material, i.e., purifying a cannabinoid. Separation can be done by a number of techniques known in the art. For example, thin layer chromatography, high performance liquid chromatography, gas chromatography, electrophoresis, microscopy, supercritical fluid chromatography, etc.

As used herein, the term "plant material" refers to matter produced by a plant of genus *cannabis*, e.g., structural materials like cellulose and/or organelles used in the plant's metabolism. In one embodiment, the plant material is a leaf. In one embodiment, the plant material is a stem. In one embodiment, the plant material is a whole ground up plant.

As used herein, the term "adding" refers to combining two or compounds together, for example when forming a composition. In one embodiment, the compounds are in a gas phase. In one embodiment, the compounds are in a liquid phase. In one embodiment, the compounds are in a solid phase. In one embodiment, the compounds are in different states of matter. For example, one compound in a solid phase is combined with another compound in a liquid phase. In one embodiment, adding comprises mixing. In one embodiment, adding comprises heating. In one embodiment, adding comprises shaking.

As used herein, the term "heating" refers to raising the temperature of a substance. In one embodiment, heating comprises applying a heat source, e.g., a lamp, a hot plate, etc. In one embodiment, heating comprises placing a substance within a heat source, e.g., placing a sample into an oven. In one embodiment, heating comprises utilizing a fire. In one embodiment, heating comprises raising the temperature of a liquid, e.g., placing a liquid in a heat proof beaker and placing the beaker onto a hot plate.

As used herein, the term "cooling" refers to lowering the temperature of a substance. In one embodiment, cooling comprises dissipating heat through stirring. In one embodiment, cooling comprises placing a substance into a refrigerator. In one embodiment, cooling comprises placing a substance into a freezer. In one embodiment, cooling comprises allowing a substance to dissipate heat through equilibrium, e.g., allowing a substance to cool to ambient temperatures.

As used herein, the term "temperature" refers to a measurement of the average kinetic energy of the atoms or molecules in a system, e.g., a confined space, e.g., a room, a cup, a container, etc. In one embodiment, temperature measures the average kinetic energy of a room. In one embodiment, temperature measures the average kinetic energy of a sample. In one embodiment, temperature is measured by a thermometer. In one embodiment, temperature is measured by a thermocouple. In one embodiment, temperature is expressed in units of Kelvin. In one embodiment, temperature is expressed in units of Fahrenheit. In one embodiment, temperature is expressed in units of Celsius. It is understood, that temperatures expressed in Kelvin, Fahrenheit, or Celsius are convertible from one another and can refer to the same desired temperature. For example, 0 degrees Celsius, 32 degrees Fahrenheit, and 273 Kelvin all approximate the freezing temperature of water.

In one embodiment, there is a first temperature.
In one embodiment, there is a first temperature is between 50-110 degrees Celsius.
In one embodiment, there is a first temperature is between 60-100 degrees Celsius.
In one embodiment, there is a first temperature is between 70-90 degrees Celsius.
In one embodiment, there is a first temperature is between 75-85 degrees Celsius.
In one embodiment, there is a second temperature.
In one embodiment, there is a first temperature is between 0-50 degrees Celsius.
In one embodiment, there is a first temperature is between 10-40 degrees Celsius.
In one embodiment, there is a first temperature is between 20-30 degrees Celsius.

In one embodiment, the methods disclosed herein comprise:
 sonicating the aqueous cannabinoid formulation comprising the mixture of Vitamin E TPGS and the first purified cannabinoid to create micelles;
 freezing the aqueous cannabinoid formulation comprising the mixture of Vitamin E TPGS and the first purified cannabinoid;
 lowering pressure of the aqueous cannabinoid formulation comprising the mixture of Vitamin E TPGS and the first purified cannabinoid; and removing water from the aqueous cannabinoid formulation comprising the mixture of Vitamin E TPGS and the first purified cannabinoid to create a dry powder.

As used herein, the term "sonicating" refers to applying sound energy. The chemical effects of sonic waves on chemical systems is called sonochemistry. Sonicating can be used for a variety of purposes, including, but is not limited to, producing nanoparticles, speeding dissolution, and/or disrupting biological material. Many variables, including the power, speed, and ratio of ingredients, can affect the properties of the resulting product. In one embodiment, the power of the sound energy applied can determine the size of micelles and/or reverse micelles.

As used herein, the term "freezing" refers to transforming a liquid or gas into a solid. In one embodiment, freezing comprises falling below a freezing point. In one embodiment, freezing comprises molecules gathering into clusters forming a crystal structure and growing continuously. In one embodiment, freezing comprises an exothermic process through the release of heat and pressure.

As used herein, the term "lowering the pressure" refers decreasing the force acting on an unit of area or increasing the area a force is acting on. In one embodiment, pressure is defined as force per unit area. In one embodiment, lowering pressure comprises keeping the force constant while increasing the area. In one embodiment, lowering the pressure comprises keeping the area constant while the force decreases. In one embodiment, pressure is expressed in pascals (Pa). In one embodiment, pressure is expressed in torres (Torr). In one embodiment, pressure is expressed in barye (Ba). In one embodiment, pressure is expressed in standard atmospheres (atm).

In some contexts, the word pressure refers to the vapor or equilibrium vapor pressure. Vapor pressure is the pressure exerted by vapor in thermodynamic equilibrium with its condensed phases, either solid or liquid, at a given temperature in a closed system.

As used herein, the term "removing water" refers to eliminating water from a composition such that the composition is substantially free from water. In one embodiment, the composition is 90% free from water. In one embodiment, the composition is 95% free from water. In one embodiment, the composition is 99% free from water. In one embodiment, removing water comprises heating the aqueous cannabinoid formulation. In one embodiment, removing water comprises drying the aqueous cannabinoid formulation for example, by applying a material that absorbs. In one embodiment, removing water comprises applying a vacuum to the aqueous cannabinoid formulation. In one embodiment, removing water comprises suctioning the aqueous cannabinoid formulation. In one embodiment, removing water comprises exposing the aqueous cannabinoid formulation to a desiccant.

In one embodiment, the method disclosed herein comprises adding water to the mixture of Vitamin E TPGS and purified cannabinoid to create an aqueous cannabinoid formulation comprising Vitamin E TPGS and between 1 to 50 mg of purified cannabinoid per mL of water.

In one embodiment, the method disclosed herein comprises adding water to the mixture of Vitamin E TPGS and purified cannabinoid to create an aqueous cannabinoid formulation comprising Vitamin E TPGS and between 5 to 20 mg of purified cannabinoid per mL of water.

In one embodiment, the method disclosed herein comprises adding water to the mixture of Vitamin E TPGS and purified cannabinoid to create an aqueous cannabinoid formulation comprising Vitamin E TPGS and between 10 to 15 mg of purified cannabinoid per mL of water.

In one embodiment, the method disclosed herein comprises adding between 5 to 20 mg of purified cannabinoid per mL of water.

In one embodiment, the method disclosed herein comprises adding between 6 to 18 mg of purified cannabinoid per mL of water.

In one embodiment, the method disclosed herein comprises adding between 8 to 15 mg of purified cannabinoid per mL of water.

In one embodiment, the method disclosed herein comprises adding between 10 to 12 mg of purified cannabinoid per mL of water.

In one embodiment, the method disclosed herein comprises sonicating the aqueous cannabinoid formulation of Vitamin E TPGS and purified cannabinoid for about 5 to 60 minutes.

In one embodiment, the method disclosed herein comprises sonicating the aqueous cannabinoid formulation of Vitamin E TPGS and purified cannabinoid for about 10 to 45 minutes.

In one embodiment, the method disclosed herein comprises sonicating the aqueous cannabinoid formulation of Vitamin E TPGS and purified cannabinoid for about 15 to 30 minutes.

In one embodiment, the method disclosed herein comprises sonicating the aqueous cannabinoid formulation of Vitamin E TPGS and purified cannabinoid for about 20 to 25 minutes.

In one embodiment, the micelles in the compositions disclosed herein are reverse micelles.

In one embodiment, the method disclosed herein comprises freezing the aqueous cannabinoid formulation, by lowering temperature to less than −20 degrees Celsius.

In one embodiment, the method disclosed herein comprises freezing the aqueous cannabinoid formulation, by lowering temperature to between 5 to −20 degrees Celsius.

In one embodiment, the method disclosed herein comprises freezing the aqueous cannabinoid formulation, by lowering temperature to between 0 to −30 degrees Celsius.

In one embodiment, the method disclosed herein comprises freezing the aqueous cannabinoid formulation, by lowering temperature to between −10 to −40 degrees Celsius.

In one embodiment, the method disclosed herein comprises freezing the aqueous cannabinoid formulation, by lowering temperature to between −20 to −50 degrees Celsius.

In one embodiment, the method disclosed herein comprises lowering the pressure of the aqueous cannabinoid formulation to less than 100 Torr.

EXAMPLES

The following examples are for illustrative purposes and not meant to be limiting.

Example 1

THC was purified, via chromatography, from a plant of genus *cannabis*, resulting in a clear, slightly yellow oil. The oil weighed 5.00 g. In a separate container 20.0 g of Vitamin E TPGS was measured. Both compounds were combined in a container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 2

CBD was purified, via chromatography, from a plant of genus *cannabis*, resulting in a clear, slightly yellow oil. The oil weighed 5.00 g. In a separate container 20.0 g of Vitamin E TPGS was measured. Both compounds were combined in a container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 3

THCV was purified, via chromatography, from a plant of genus *cannabis*, resulting in a clear, slightly yellow oil. The oil weighed 5.00 g. In a separate container 20.0 g of Vitamin E TPGS was measured. Both compounds were combined in a container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 4

THC, CBD, and CBGV were purified, via chromatography, from a plant of genus *cannabis*, resulting in a clear, slightly yellow oil. The oil weighed 5.00 g. In a separate container 20.0 g of Vitamin E TPGS was measured. Both compounds were combined in a container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 5

THC, CBD, and THCV were purified, via chromatography, from a plant of genus *cannabis*, resulting in a clear, slightly yellow oil. Alpha-Pinene, Alpha-Humulene, and Terpinolene were each purified from plant matter via chromatography. The purified terpenes were added to the cannabis oil. The final cannabinoid and terpene oil weighed 5.00 grams. In a separate container 20.0 g of Vitamin E TPGS was measured. The cannabinoid and terpene oil and Vitamin E TPGS were combined in a separate container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 6

THC, CBD, and THCV were purified, via chromatography, from a plant of genus *cannabis*, resulting in a clear, slightly yellow oil. Linalool, Alpha-Pinene, Eucalyptol, Pulegone and Terpinolene were each purified from plant matter via chromatography. The purified terpenes were added to the cannabis oil. The final cannabinoid and terpene oil weighed 5.00 grams. In a separate container 20.0 g of Vitamin E TPGS was measured. The cannabinoid and terpene oil and Vitamin E TPGS were combined in a separate container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 7

THC, CBD, and THCV were purified, via chromatography, from a plant of genus *cannabis*, resulting in a clear, slightly yellow oil. Beta-Caryophyllene, Linalool, and Terpineol were each purified from plant matter via chromatography. The purified terpenes were added to the cannabis oil. The final cannabinoid and terpene oil weighed 5.00 grams. In a separate container 20.0 g of Vitamin E TPGS was measured. The cannabinoid and terpene oil and Vitamin E TPGS were combined in a separate container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 8

THC, CBD, and THCV were purified, via chromatography, from a plant of genus *cannabis*, resulting in a clear, slightly yellow oil. Beta-Caryophyllene, Linalool, and Cymene were each purified from plant matter via chromatography. The purified terpenes were added to the cannabis oil. The final cannabinoid and terpene oil weighed 5.00 grams. In a separate container 20.0 g of Vitamin E TPGS was measured. The cannabinoid and terpene oil and Vitamin E TPGS were combined in a separate container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 9

THC, CBD, and THCV were purified, via chromatography, from a plant of genus *cannabis*, resulting in a clear, slightly yellow oil. Alpha-Pinene, Linalool, Cymene, and Terpineol were each purified from plant matter via chromatography. The purified terpenes were added to the cannabis oil. The final cannabinoid and terpene oil weighed 5.00 grams. In a separate container 20.0 g of Vitamin E TPGS was measured. The cannabinoid and terpene oil and Vitamin E TPGS were combined in a separate container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 10

THCA, CBC, THC, CBN, CBD, CBG, CBGA, and CBDA were purified, via chromatography, from a plant of genus *cannabis*, resulting in a clear, slightly yellow oil. The cannabinoid oil weighed 5.00 grams. In a separate container 20.0 g of Vitamin E TPGS was measured. The cannabinoid and terpene oil and Vitamin E TPGS were combined in a separate container with 50 mL of water. The solution was sonicated for 15-20 minutes until a homogeneous mixture was formed.

The solution was transferred to a tray, forming a thin layer of about 2 cm in depth. The tray was then placed in a freezer for 8 hours resulting in a solid sheet. The solid sheet was placed in a plastic bag and vacuumed sealed under reduced pressure for one hour. The tray was removed from the bag and placed in an oven for 1 hour. The tray cooled to ambient temperature and then the thin layer was scraped with a scraper to afford a powder. If clumping occurred, a mortar and pestle was used to make a finer powder. The micelles were measured with a refractometer.

Example 11

THC was purified, via chromatography, from a plant of genus *cannabis*, resulting in a clear, slightly yellow oil. The oil weighed 5.00 g. In a separate container 20.0 g of Vitamin E TPGS was measured. Both compounds were combined in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 12

CBD was purified, via chromatography, from a plant of genus *cannabis*, resulting in a clear, slightly yellow oil. The oil weighed 5.00 g. In a separate container 20.0 g of Vitamin E TPGS was measured. Both compounds were combined in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 13

THCV was purified, via chromatography, from a plant of genus *cannabis*, resulting in a clear, slightly yellow oil. The oil weighed 5.00 g. In a separate container 20.0 g of Vitamin E TPGS was measured. Both compounds were combined in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 14

THC, CBD, and CBGV were purified, via chromatography, from a plant of genus *cannabis*, resulting in a clear, slightly yellow oil. The oil weighed 5.00 g. In a separate container 20.0 g of Vitamin E TPGS was measured. Both compounds were combined in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 15

THC, CBD, and THCV were purified, via chromatography, from a plant of genus *cannabis*, resulting in a clear, slightly yellow oil. Alpha-Pinene, Alpha-Humulene, and Terpinolene were each purified from plant matter via chromatography. The purified terpenes were added to the cannabis oil. The final cannabinoid and terpene oil weighed 5.00 grams.

In a separate container 20.0 g of Vitamin E TPGS was measured. The cannabinoid and terpene oil was combined with Vitamin E TPGS in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 16

THC, CBD, and THCV were purified, via chromatography, from a plant of genus *cannabis*, resulting in a clear, slightly yellow oil. Linalool, Alpha-Pinene, Eucalyptol, Pulegone and Terpinolene were each purified from plant matter via chromatography. The purified terpenes were added to the cannabis oil. The final cannabinoid and terpene oil weighed 5.00 grams.

In a separate container 20.0 g of Vitamin E TPGS was measured. The cannabinoid and terpene oil was combined with Vitamin E TPGS in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 17

THC, CBD, and THCV were purified, via chromatography, from a plant of genus *cannabis*, resulting in a clear, slightly yellow oil. Beta-Caryophyllene, Linalool, and Terpineol were each purified from plant matter via chromatography. The purified terpenes were added to the cannabis oil. The final cannabinoid and terpene oil weighed 5.00 grams.

In a separate container 20.0 g of Vitamin E TPGS was measured. The cannabinoid and terpene oil was combined with Vitamin E TPGS in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 18

THC, CBD, and THCV were purified, via chromatography, from a plant of genus *cannabis*, resulting in a clear, slightly yellow oil. Beta-Caryophyllene, Linalool, and Cymene were each purified from plant matter via chromatography. The purified terpenes were added to the cannabis oil. The final cannabinoid and terpene oil weighed 5.00 grams.

In a separate container 20.0 g of Vitamin E TPGS was measured. The cannabinoid and terpene oil was combined with Vitamin E TPGS in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 19

THC, CBD, and THCV were purified, via chromatography, from a plant of genus *cannabis*, resulting in a clear, slightly yellow oil. Alpha-Pinene, Linalool, Cymene, and Terpineol were each purified from plant matter via chromatography. The purified terpenes were added to the cannabis oil. The final cannabinoid and terpene oil weighed 5.00 grams.

In a separate container 20.0 g of Vitamin E TPGS was measured. The cannabinoid and terpene oil was combined with Vitamin E TPGS in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Example 20

THCA, CBC, THC, CBN, CBD, CBG, CBGA, and CBDA were purified, via chromatography, from a plant of genus *cannabis*, resulting in a clear, slightly yellow oil. The oil weighed 5.00 grams.

In a separate container 20.0 g of Vitamin E TPGS was measured. The cannabinoid oil was combined with Vitamin E TPGS in a heat proof beaker and placed on a hot plate. The mixture was heated to 80 degrees Celsius. After the mixture reached 80 degrees Celsius, water was added while stirring until the mixture turned into a viscous, amorphous mass. The beaker was removed from the hot plate and the mixture allowed to cool to room temperature while stirring resulting in an aqueous solution.

Although the present invention herein has been described with reference to various exemplary embodiments, it is to be understood that these embodiments are merely illustrative of the principles and applications of the present invention. Those having skill in the art would recognize that various modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

Finally, it is noted that, as used in this specification and the appended claims, the singular forms "a," "an," and "the," include plural referents unless expressly and unequivocally limited to one referent, and vice versa. As used herein, the term "include" or "comprising" and its grammatical variants are intended to be non-limiting, such that recitation of an item or items is not to the exclusion of other like items that can be substituted or added to the recited item(s).

What is claimed is:

1. A water-soluble powder composition, comprising:
   one or more purified cannabinoids;
   a purified terpene; and
   Vitamin E TPGS.

2. The composition of claim 1, comprising a ratio of Vitamin E TPGS to the one or more purified cannabinoids of about 85:15 to about 75:25 by percent mass.

3. The composition of claim 1, comprising a ratio of Vitamin E TPGS to the one or more purified cannabinoids of about 82:18 to about 78:22 by percent mass.

4. The composition of claim 1, comprising between 0-1% water by mass percent.

5. The composition of claim 4, comprising between 0-0.5% water by mass percent.

6. The composition of claim 1, wherein the one or more purified cannabinoids is Cannabidiol (CBD), Tetrahydrocannabinol (THC), Tetrahydrocannabivarin (THCV) or a combination thereof.

7. The composition of claim 6, wherein the composition comprises the combination of THC, CBD and THCV.

8. The composition of claim 1, wherein the purified terpene is linalool, alpha-pinene, alpha-humulene, terpinolene, eucalyptol, pulegone, terpineol, beta-caryophyllene, cymene or combinations thereof.

9. The composition of claim 7, wherein the composition comprises the combination of beta-caryophyllene, linalool, and cymene as purified terpenes.

10. A method of making a water soluble powder comprising a first purified cannabinoid and a purified terpene, the method comprising:
    separating a first purified cannabinoid and a purified terpene from a cannabis plant material;
    combining the first purified cannabinoid and the purified terpene to form a cannabis oil;
    adding the cannabis oil and Vitamin E TPGS to water to create an aqueous cannabinoid formulation;
    sonicating the aqueous cannabinoid formulation; and
    removing the water from the aqueous cannabinoid formulation to create a water soluble powder.

11. The method of claim 10, wherein removing the water from the aqueous cannabinoid formulation comprises freeze-drying the aqueous cannabinoid formulation.

12. The method of claim 11, further comprising heating the freeze-dried aqueous cannabinoid formulation to a temperature between 70-90° C.

13. The method of claim 10, wherein the aqueous cannabinoid formulation comprises a ratio of Vitamin E TPGS to the first purified cannabinoid of about 85:15 to about 75:25 by percent mass.

14. The method of claim 10, wherein the aqueous cannabinoid formulation comprises a ratio of Vitamin E TPGS to the first purified cannabinoid of about 82:18 to about 78:22 by percent mass.

* * * * *